(12) United States Patent
Dussourd et al.

(10) Patent No.: US 6,211,155 B1
(45) Date of Patent: Apr. 3, 2001

(54) PEPTIDE CONJUGATES DERIVED FROM THYMIC HORMONES, THEIR USE AS A MEDICAMENT AND COMPOSITIONS CONTAINING THEM

(75) Inventors: Lucien Dussourd, Toulouse; Anne-Marie Pinel, La Grande Motte, both of (FR)

(73) Assignee: Institut European de Biologie Cellulaire (FR)

( * ) Notice: Subject to any disclaimer, the term of this patent is extended or adjusted under 35 U.S.C. 154(b) by 0 days.

(21) Appl. No.: 09/068,767

(22) PCT Filed: Nov. 15, 1996

(86) PCT No.: PCT/FR96/01812

§ 371 Date: Aug. 24, 1998

§ 102(e) Date: Aug. 24, 1998

(87) PCT Pub. No.: WO97/18239

PCT Pub. Date: May 22, 1997

(30) Foreign Application Priority Data

Nov. 15, 1995 (FR) .................................... 95 13544

(51) Int. Cl.[7] .......................... A61K 38/06; A61K 38/07; A61K 38/08
(52) U.S. Cl. ................................. 514/18; 514/17; 514/16; 514/15; 530/328; 530/329; 530/330; 530/331
(58) Field of Search ................................. 514/15, 16, 17, 514/18; 530/328, 329, 330, 331

(56) References Cited

U.S. PATENT DOCUMENTS 4,301,065 * 11/1981 Bach .................................. 260/112.5
5,112,810 * 5/1992 Nagai ...................................... 514/15

FOREIGN PATENT DOCUMENTS 0 166 612 A2 * 1/1986 (EP) .
0 166 612 1/1986 (EP) .
2 411 174 7/1979 (FR) .

OTHER PUBLICATIONS

Heavner et al., Biologically Active Analogs of Thymopentin with Enhanced Enzymatic Stability, Peptides, vol. 7 pp. 1015–1019, 1986.*
Heavner et al., "Peptide analogs of thymopentin distinguish distinct thymopoietin receptor specificities on two human T cell lines", Reg. Peptides, 27:257–262 (1990).
Heavner et al., "Biologically Active Analogs of Thymopentin With Enhanced Enzymatic Stability", Peptides, 7:1015–1019 (1986).
Chemical Abstracts, "Peptides for radioimmunoassay of serum thymic factor", vol. 104, No. 3, Abstract No. 19826 (1986).
Chemical Abstracts, "Histamine–releasing activity as an undesired side–effect in the development of peptide analogs", vol. 122, No. 1, Abstract No. 1237g (1995).

* cited by examiner

*Primary Examiner*—F. T. Moezie
(74) *Attorney, Agent, or Firm*—Finnegan, Henderson, Farabow, Garrett & Dunner, L.L.P.

(57) ABSTRACT

The invention relates to peptide conjugates comprising a sequence of at least 3 amino acids derived from a thymic hormone selected amongst thymuline and thymopoietine, the amino acids being independently in the form D, L or DL, said sequence being chemically or physically conjugated with at least one compound selected amongst monocarboxylic acids having the general formula (I): HOOC—R, as well as alcohol, aldehyde or amide derivatives, the dicarboxylic acids having the general formula (II): HOOC—$R_1$—COOH. The invention also relates to the use of such conjugates as medicaments, and pharmaceutical or cosmetological compositions containing them.

28 Claims, 7 Drawing Sheets

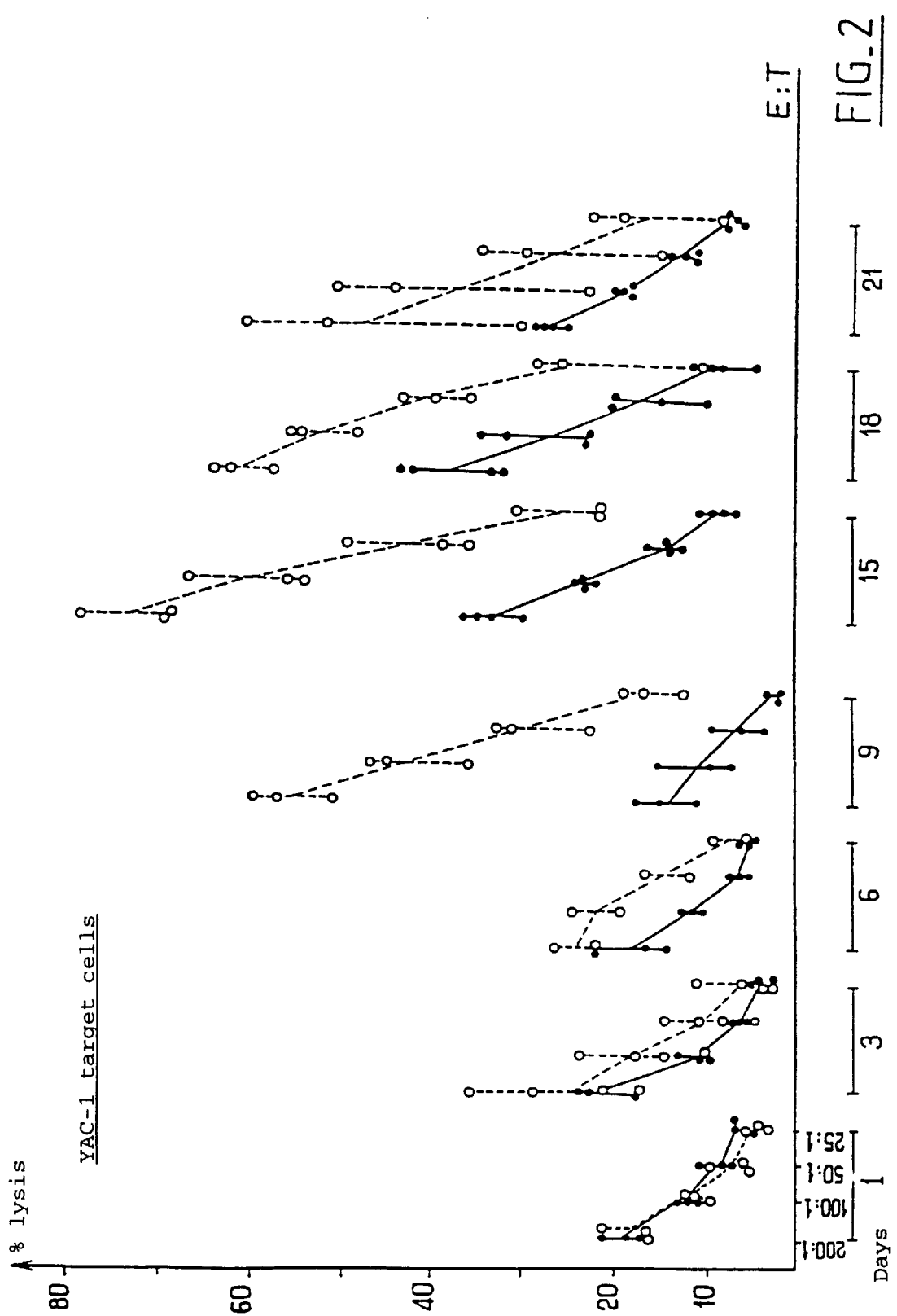
FIG_2

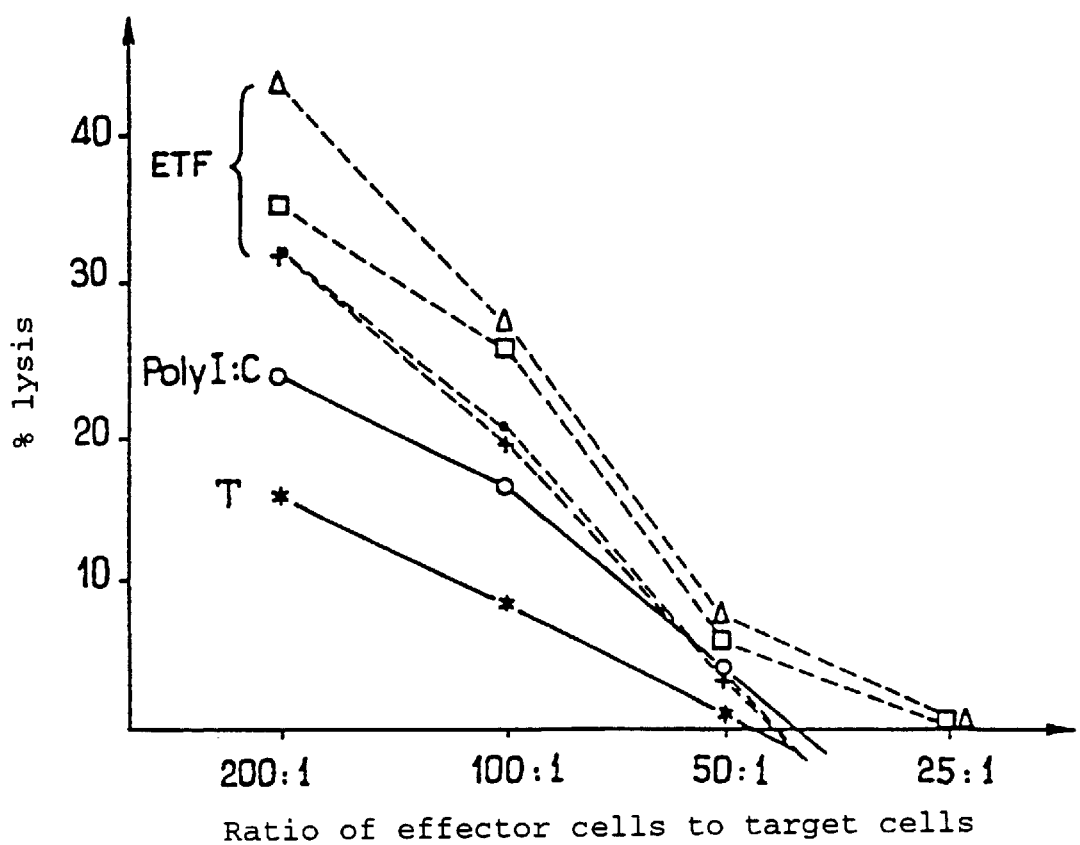
FIG_4

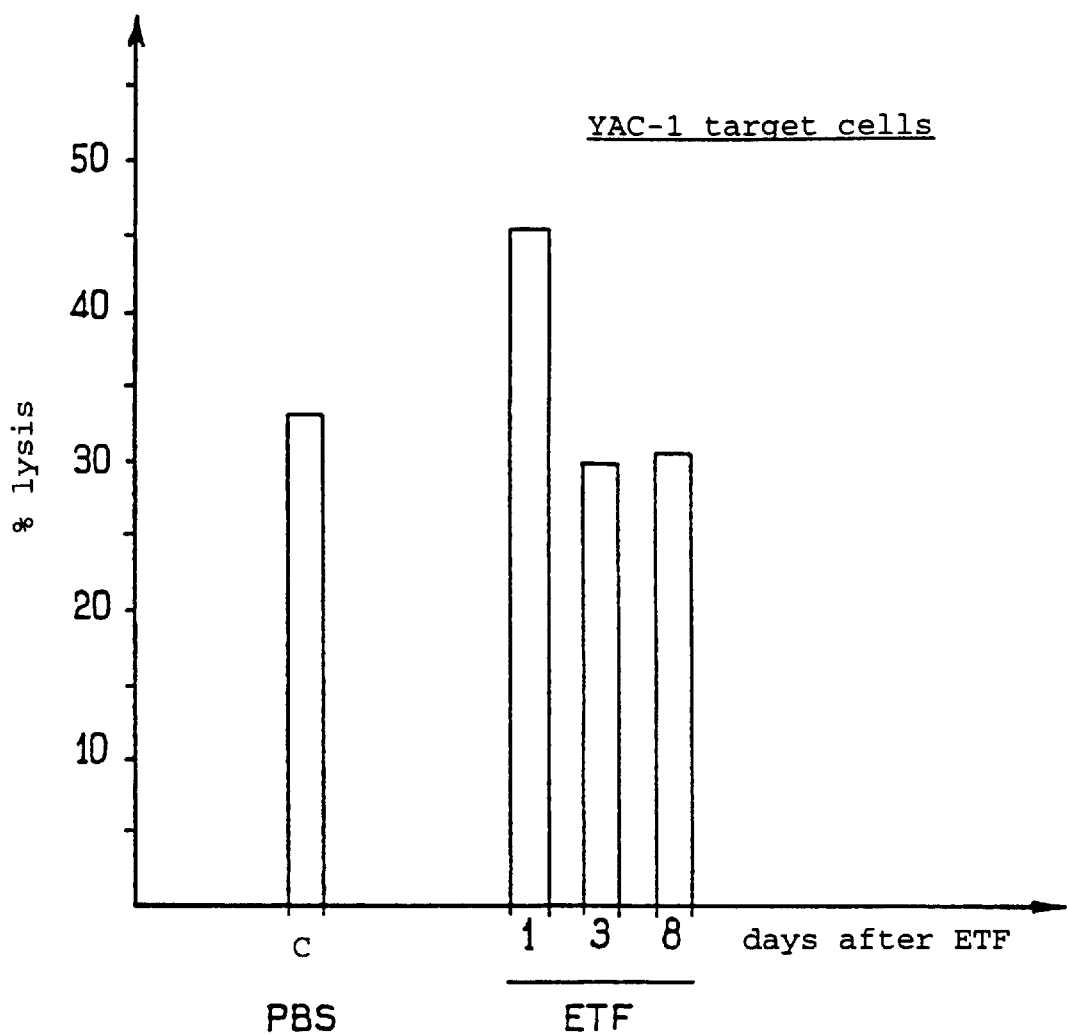
FIG_7

PEPTIDE CONJUGATES DERIVED FROM THYMIC HORMONES, THEIR USE AS A MEDICAMENT AND COMPOSITIONS CONTAINING THEM

CROSS-REFERENCES TO RELATED APPLICATIONS

This application is a National Stage application of International Application No. PCT/FR96/01812 filed Nov. 15, 1996.

BACKGROUND OF THE INVENTION

The invention relates to novel synthetic derivatives of two thymic hormones, i.e. thymulin and thymosin, and to their uses as a medicament or in the field of cosmetology.

The large number of studies which have been carried out on the functioning of the immune system have demonstrated the cardinal role played by the thymus and the thymic hormones in stimulating the immune defences of the organism.

The thymic hormones, in particular thymulin, "J. F. Bach et al.", thymopoietin "Grandstein" and thymosin "Dayne" have been identified as being of a polypeptide or peptide nature.

These hormones, principally thymulin and thymopoietin, possess the property of inducing maturation of the T lymphocytes and of stimulating the immune response of the organism.

It has been scientifically demonstrated that a close relationship exists between the decrease in thymic functions with age and cutaneous ageing under normal physiological circumstances.

At a pathological level, the loss of thymic activity, i.e. "involution", finds expression in the appearance of physiological disorders: "autoimmune diseases, alopecias (abnormal hair loss), etc.".

It has also been shown that a relationship exists between the physiological properties of the thymus and certain cells of the epidermis.

Thus, a structural similarity exists between certain cells of the thymus and keratinocytes. It has also been shown that, under certain conditions, the keratinocytes also secrete a hormone of the thymopoietin type which is identical to that secreted by the thymus and are able to induce post-thymic lymphocyte maturation and in this way to take over from the thymus.

This relationship between the physiological activities of the cells of the thymus and the keratinocytes has recently been confirmed by demonstrating that keratin and keratohyalin, which have identical structures to those of the keratin and keratohyalin which are secreted by the epidermal keratinocytes, are present in the cells of the thymus.

Furthermore, the scientific demonstration that keratinocytes which are in the differentiation phase secrete a substance, i.e. ETAF, which activates thymocyte growth, confirms the physiological relationships which exist between the thymus and the keratinocytes. (ETAF: epidermal thymocyte activating factor).

A parallel exists between the "involution" of the thymus and the decrease in the synthesis of ETAF by the keratinocytes as a function of age, with, however, a functional time-lag in favour of the keratinocytes (post-thymic lymphocyte maturation).

The thymic hormones, in particular thymulin and thymopoietin, have been used therapeutically in a large number of pharmacological and clinical studies with the aim in view of stimulating and regulating the immune defenses of the organism.

When used in the form of extracts or of molecules obtained by chemical synthesis, these products have yielded variable and disappointing results as a result of their lack of stability and a ubiquitous effect linked to the absence of dose-effect relationships.

SUMMARY OF THE INVENTION

The present invention relates to using chemical synthesis to obtain peptide derivatives of the thymic hormones, the structure of which derivatives has been adjusted so as to provide the derivatives with a high degree of physicochemical stability and a precisely defined pharmacological activity.

Using all the knowledge which our research groups have recently acquired and developed concerning the essential role of the epidermis in immune defense and its relationships with the thymus (International Society of Development and Comparative Immunology), the present invention relates to the creation of synthetic peptide derivatives whose physiological and therapeutic activity is directed toward stimulating and modulating the immune defenses of the corium and the epidermis in preference to any systemic action.

In one aspect, the invention preferably relates to using chemical synthesis to create metallopeptides whose physiological properties are specifically directed toward activating the cutaneous immune system and stimulating the germinative functions of the basal cells of the epidermis to the exclusion of any secondary effect on systemic (general) immunity.

The present invention relates to the creation of peptide molecules which are homologs or derivatives of the active peptide sequences of the principal thymic hormones, i.e. thymulin and thymopoietin.

The large number of clinical tests which have been carried out using these hormonal mediators have failed to demonstrate that these mediators have any therapeutic relevance.

Thus, when these hormones have been used in the form of injectable preparations for treating immune deficiencies and autoimmune disorders, the results obtained have all been negative because of the ubiquitous activity of the hormones in terms of the doses administered.

It appears that these ubiquitous effects are linked to the structure of these compounds which results from synthesis and which does not enable them to bind normally to globulins and cell receptors, taking into account the fact that they are administered parenterally.

For this reason, one aspect of the invention relates to creating compounds in the form of metallopeptides which are obtained by synthesis and whose physiological activities are directed toward modulating the immune system and activating the germinative cells of the epidermis, by means of local topical applications in accordance with the pharmacological principle of "structure-activity relationships" (Hänch's principle).

More specifically, the present invention relates to a pharmaceutical or cosmetological composition which contains at least one peptide conjugate which comprises a sequence of at least three amino acids which are derived from the total sequence of thymulin or of thymopoietin, with it being possible for the amino acids to be in the D, L or DL form, the said sequence being conjugated chemically or physically with at least one compound which is selected from:

monocarboxylic acids of the general formula $$HOOC-R \quad (I)$$

in which R represents a straight-chain or branched, optionally substituted $C_1$–$C_{20}$ aliphatic radical which can contain one or more unsaturations, as well as the alcohol or aldehyde or amide derivatives of the acids of the formula I;

dicarboxylic acids of the general formula $$HOOC-R_1-COOH \qquad (II)$$

in which $R_1$ represents a straight-chain or branched divalent aliphatic radical which comprises at least 3 carbon atoms, preferably from 3 to 10 carbon atoms, in particular an alkyl, alkylene, alkenylene or alkynylene radical, and which can contain one or more unsaturations and can optionally be substituted, in particular by one or more amino, hydroxyl or oxo groups or by a $C_1$–$C_3$ alkyl radical, with it also being possible for $R_1$ to form a cycle with one of the acid functions.

The conjugates according to the invention are low-molecular-weight derivatives which are obtained, in particular, in the form of salts, esters or amides of the compounds of the formula I or II.

The compounds of the formula I which are particularly preferred are carboxylic acids which have a metabolic activity which is essential for the Krebs tricarboxylic cycle and which act in the mitochondria as coenzymes of oxidative decarboxylation, and whose properties are to bind, preferably covalently, to the ε amino functions of certain peptides, in the form of lipoamides, thereby facilitating presentation of the peptide conjugates, which are obtained in accordance with the invention, to the G class β receptor of the epidermal cells.

In the case of these acids, and of others which are suitable for implementing the invention, R can represent a substituted or unsubstituted, straight-chain or branched $C_1$–$C_{20}$, in particular $C_1$–$C_4$, aliphatic radical, in particular an alkyl, alkenyl or alkynyl radical, which can contain one or more unsaturations and which can be substituted by one or more radicals which are selected from the group comprising: $NH_2$, OH, oxo or thiol or a nonaromatic cyclic radical which contains from 5 to 6 atoms in the cycle, 1 or 2 of which can be different from carbon, in particular S, O or N, with it being possible for the said cycles to be substituted by $C_1$ to $C_3$ alkyl radicals, in particular methyl.

In particular, when R represents a $C_1$–$C_{20}$ aliphatic chain, it can be substituted by a cycle which is selected from

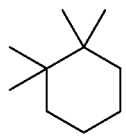 and .

Other compounds of the formula I which are suitable for implementing the invention are those in which, in the general formula I, R can represent a monounsaturated radical, having the cis or trans configuration, of the general formula $$R_2-CH=CH-$$

in which $R_2$ can represent a straight-chain or branched alkyl radical which comprises at least 6 carbon atoms, preferably from 6 to 16 carbon atoms, and which is optionally substituted by an amino, hydroxyl or oxo group.

Advantageously, in the formula II, $R_1$ represents an optionally substituted $C_4$–$C_8$ alkylene radical.

Peptide conjugates according to the invention are, in particular, those in which the acid of the general formula I is selected from acetic acid, pyroglutamic acid, DL-lipoic acid, dihydrolipoic acid, N-lipoyllysine, hydroxydecenoic and decenoilic acids, retinoic acid and its derivatives, retinal and retinol, myristic acid and its derivatives, palmitic acid, in the form of salts, esters or amides, or else the acid of the general formula II is selected from adipic acid, α-aminoadipic acid, pimelic acid or sebacic acid, and their derivatives.

The acids of the general formulae I or II are preferably selected from acetic acid and its derivatives, pyroglutamic acid, α-DL-lipoic acid and its derivatives, dihydrolipoic acid, N-lipoyllysine, adipic acid, α-aminoadipic acid, pimelic acid, sebacic acid and its derivatives, trans-10-hydroxy-Δ2-decenoic acid and trans-9-oxo-2-decenoic acid, retinoic acid and its derivatives, retinol and retinal, myristic acid and palmitic acid.

The amino acid sequence of the conjugates according to the invention will contain one of the following 3 sequences:

Gln-Gly-Gly

Arg-Lys-Asp

Lys-Asp-Val

Thus, more specifically, the present invention relates to the creation of two series of peptide molecules, whose activities are complementary, for use in the fields of human medicine and dermocosmetology.

The present invention preferably relates to peptide conjugates which are derived from circulating thymic hormone, i.e. thymulin, and whose physiological activities are directed toward effecting maturation of the immune system and of the different mediators of the cutaneous immune system.

Thus, these peptide conjugates are particularly directed toward treating autoimmune diseases of the skin, and in particular preventing and treating alopecias whether they be of physiological (aging), traumatic or pathological origin.

The present invention also relates to creating peptide conjugates which are derived from cellular thymic hormone, i.e. thymopoietin, and whose physiological activities are also directed toward effecting maturation of the immune system of the skin while possessing a preferential activity for stimulating the metabolism of the cells of the epidermis, in particular of the germinative keratinocytes, in which latter they stimulate both secretion formation and the intracellular synthesis of the "low-molecular-weight keratin and keratohyalin" structural molecules.

Thus, this series of peptide conjugates is particularly indicated for the treatment of disorders of the skin which are linked to immune deficiencies and, in particular, for the prophylactic or therapeutic treatment of cutaneous ageing which is of a physiological (age) or pathological nature.

Preferably, the amino acid sequence of the peptide conjugates which are derived from thymulin corresponds to the following general formula:

X-Gln-Gly-Gly-Y (SEQ ID NO:1)

in which Gln represents glutamine or a derivative of glutamine, Gly represents glycine or a derivative of glycine; the derivatives include, in particular, the halogenated derivatives of the amino acids in question. The amino acids can be in a natural or unnatural form.

According to one of the aspects of the invention, the peptide conjugates will therefore have the following formula:

A-X-Gln-Gly-Gly-Y (SEQ ID NO:1)     (III)

in which A is a compound of the general formula I or II, as previously defined, in particular DL-lipoic acid, dihydrolipoic acid or N-lipoyllysine.

X is:
    Ser, Lys-Ser, Ala-Lys-Ser, Pyr-Ala-Lys-Ser (SEQ ID NO:2), a bond
    bond or Glx-Ala-Lys-Ser (SEQ ID NO:3)
    in which Glx is: Pyr-Glu, Glu or Gly and its derivatives
Y is:
    Ser-Asn-OH
    Ser-Asn-NH2
    Ser-OH
    Ser-NH2
with the amino acids being in the L, D or DL form.

In the formulae which follow, Pyr represents pyroglutamic acid.

The peptide conjugates of the formula III preferably include a sequence of at least 4 amino acids, in particular of from 4 to 9 amino acids, with this sequence advantageously comprising the sequence Gln-Gly-Gly-Ser.

The present invention very specifically relates to the following conjugates:

| | | |
|---|---|---|
| I | A-Pyr-Ala-Lys-Ser-Gln-Gly-Gly-Ser-Asn-NH$_2$ | (SEQ ID NO:5) |
| II | A-Pyr-Ala-Lys-Ser-Gln-Gly-Gly-Ser-NH$_2$ | (SEQ ID NO:6) |
| III | A-Ala-Lys-Ser-Gln-Gly-Gly-Ser-Asn-NH$_2$ | (SEQ ID NO:7) |
| IV | A-Ala-Lys-Ser-Gln-Gly-Gly-Ser-NH$_2$ | (SEQ ID NO:8) |
| V | A-Lys-Ser-Gln-Gly-Gly-Ser-Asn-NH$_2$ | (SEQ ID NO:9) |
| VI | A-Lys-Ser-Gln-Gly-Gly-Ser-NH$_2$ | (SEQ ID NO:10) |
| VII | A-Ser-Gln-Gly-Gly-Ser-Asn-NH$_2$ | (SEQ ID NO:11) |
| VIII | A-Ser-Gln-Gly-Gly-Ser-NH$_2$ | (SEQ ID NO:10) |
| IX | A-Gln-Gly-Gly-Ser-Asn-NH$_2$ | (SEQ ID NO:10) |
| X | A-Gln-Gly-Gly-Ser-NH$_2$ | (SEQ ID NO:10) |
| XXIII | A-Ala-Lys-Ser-Gln-Gly-Gly-Ser-Asn-OH | (SEQ ID NO:26) | with A having been defined previously, as well as to the derivatives of these molecules in the form of salts, esters or amides.

The abovementioned amino acid sequences can be obtained in the terminal NH$_2$ form and in the terminal OH form.

Similarly, it is possible, in some cases, for some of these amino acids to possess functions, for example glycosylations.

According to another aspect, the invention relates to peptide conjugates which are derived from thymopoietin and which correspond to the following general formula:

A-W-Lys-Asp-Z (SEQ ID NO:15)    (IV)

in which A is a compound of the general formula I or II, as previously defined, or the corresponding radical, in particular acetic acid and its derivatives, DL-α-lipoic acid and its derivatives, dihydrolipoic acid, N-lipoyllysing, adipic acid, α-aminoadipic acid, pimelic acid, sebacic acid and its derivatives, trans-9-oxo-2-decenoic acid or trans-10-hydroxy-2-decenoic acid.

```
W represents: Glu-Gln-Arg, Gln-Arg, Arg,
              Arg-Lys-, Arg-Lys-Asp or a bond
Z represents: Val-Tyr-NH2, Val-Tyr-OH
              Val-NH2, Val-OH, Tyr-OH, Tyr-NH2,
              OH or NH2
``` with W and Z being selected such that at least one of the sequences Arg-Lys-Asp or Lys-Asp-Val is present in the compounds of the formula IV.

Peptide conjugates of the formula IV which include the sequence Arg-Lys-Asp-Val (SEQ ID NO:16) yield excellent results.

The amino acids can be in the D, L or DL form and can, where appropriate, by glycosylated.

The following conjugates of the formula IV are peptide conjugates which are particularly suitable and whose biological activities are complementary to those of the peptide conjugates of the formula III:

| | | |
|---|---|---|
| XI | A-Glu-Gln-Arg-Lys-Asp-Val-Tyr-NH$_2$ | (SEQ ID NO:17) |
| XII | A-Glu-Gln-Arg-Lys-Asp-Val-Tyr-OH | (SEQ ID NO:17) |
| XIII | A-Gln-Arg-Lys-Asp-Val-Tyr-NH$_2$ | (SEQ ID NO:18) |
| XIV | A-Gln-Arg-Lys-Asp-Val-Tyr-OH | (SEQ ID NO:18) |
| XV | A-Arg-Lys-Asp-Val-Tyr-NH$_2$ | (SEQ ID NO:19) |
| XVI | A-Arg-Lys-Asp-Val-Tyr-OH | (SEQ ID NO:19) |
| XVII | A-Lys-Asp-Val-Tyr-NH$_2$ | (SEQ ID NO:20) |
| XVIII | A-Lys-Asp-Val-Tyr-OH | (SEQ ID NO:20) |
| XIX | A-Arg-Lys-Asp-Val-NH$_2$ | (SEQ ID NO:21) |
| XX | A-Arg-Lys-Asp-Val-OH | (SEQ ID NO:21) |
| XXI | A-Arg-Lys-Asp-NH$_2$ | |
| XXII | A-Arg-Lys-Asp-OH | | with "A" being as previously defined, as are the derivatives of these molecules in the form of salts, esters or amides.

The abovementioned amino acid sequences can be sequences of natural or unnatural amino acids.

It is hereby pointed out that the abovementioned peptide conjugates can be obtained in the NH$_2$-terminal or OH-terminal form.

The peptide conjugates according to the invention can also be present in the form of molecular complexes with a metal, in particular zinc.

The conjugates according to the invention can be obtained by synthesis, using techniques known to the skilled person.

The free peptides can be synthesized by the MERRIFIELD techniques, using two methods.

In the first method, a glutamine derivative is used whose γ amide function is protected with "Mbh", i.e. 4,4-dimethoxybenzhydryl.

In the second method, the synthesis is carried out without protecting the γ amide of the glutamine residues.

When the first procedure and the second procedure are used, the protected C-terminal part of the dipeptide is respectively linked to the protected tetrapeptide Ser-Gln-Gly and to the protected hexapeptide Ala-Lys-Gln-Gly-Gly (SEQ ID NO:22).

Thus, the polypeptides of the sequence

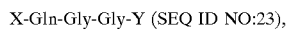
X-Gln-Gly-Gly-Y (SEQ ID NO:23), in which Y represents Ser-Asn and X represents Ser or Ala-Lys-Ser, are prepared by linking the protected dipeptide Ser-Asn to the protected peptide X-Gln-Gly-Gly and possibly consecutively eliminating the protecting groups.

Therefore, the octapeptide Ala-Lys-Ser-Gln-Gly-Gly-Ser-Asn (SEQ ID NO:14) is obtained when the second procedure is used while the same octapeptide is prepared from the hexapeptide Ser-Gln-Gly-Gly-Ser-Asn (SEQ ID NO:11), by way of the heptapeptide Lys-Ser-Gln-Gly-Gly-Ser-Asn (SEQ ID NO:9), when the first procedure is used.

The octapeptide Ala-Lys-Ser-Gln-Gly-Gly-Ser-Asn (SEQ ID NO:14) then enables the two forms to be prepared by adding on the first residue, i.e. PyroGlu or Gln.

The process employed for adding the PyroGlu residue onto the sequence Ala-Lys-Ser-Gln-Gly-Gly-Y (SEQ ID NO:24) is the same whatever the possible meanings of Y, namely Ser and Ser-Asn, and the possible meanings which are derived therefrom by altering an amino acid, for example in the case of Ser-Asp or Ala-Asn (SEQ ID NO:24).

This addition to the sequence Ala-Lys-Ser-Gln-Gly-GLy-Y is advantageously obtained using the derivative PyrGlu-OTcp, with it being possible for the side chain functions of certain amino acids in the sequence to be protected.

The peptide derivatives to which the present invention relates, and which have been described previously, can be used in their peptide form or in the form of conjugates with the previously described carboxylic acids which correspond to the general formula I.

The same peptide conjugates can be used in the form of molecular complexes with a metal.

The metal employed for preparing the metallopeptide complexes of the present invention is, for example, zinc, in the form of $ZnCl_2$, which can be coupled, in salt form, to a carboxylic group of the terminal amino acid, or in the form of "$Zn^2$-peptide" complexes in the following proportions of 0.5 to 5%, preferably 1%, of $ZnCl_2$ per peptide molecule.

These proportions are variable depending on the molecular weight of the peptide conjugate.

The metallopeptide complex can, in particular, be obtained in a 10% $ZnCl_2$ solution, for one peptide molecule, after heating at 20° C. for 10 minutes.

The complex is then purified, for example on a P-2 biogel column, and eluted with distilled water, after which it is lyophilized.

A stable colyophilizate is obtained which contains 1% zinc bound by affinity to the peptide molecule.

All of the compounds according to the present invention can be used as medicaments.

In particular, the conjugates according to the present invention can be used for preparing a medicament which is intended for correcting deficiencies of the immune system.

The pharmaceutical compositions can comprise at least one conjugate according to the invention and excipients which are suitable for administration by the parenteral route or by the external topical route.

These compositions can be used in the fields of both human medicine and veterinary medicine; while they can be administered by the oral route or the parenteral route, they are preferably in a form which can be administered by the external topical route.

Compositions which are particularly suitable for implementing the invention are those which comprise one of the following conjugates:

acetic acid-Arg-Lys-Asp-Val-Tyr-NH$_2$ (SEQ ID NO:19)
   Pyr-Ala-Lys-Ser-Gln-Gly-Gly-Ser-Asn-OH (SEQ ID NO:25)

where appropriate in the form of a complex with a metal.

The peptide conjugates to which the invention relates, their derivatives and their pharmaceutical compositions can be in the form of creams, milks, lotions appropriate, other active principles.

They can be used alone or in the form of pharmaceutical combinations or compositions for treating autoimmune disorders in the different fields of dermatology.

The invention also relates to the use of the peptide conjugates in dermocosmetology and in cosmetology.

The present invention therefore relates to galenic, pharmaceutical and cosmetological compositions which comprise at least one of the previously described peptide conjugates.

The peptide conjugates of the invention, their derivatives and their combinations with known active principles can be used in the form of cosmetological and capillary preparations, in particular for rejuvenating and renewing the superficial layers of the skin and, in particular, for the cosmetocapillary treatment of hair loss.

BRIEF DESCRIPTION OF THE DRAWINGS

FIG. 2: effect of ETF, administered by the topical route, on NK cells (target cells: YAC1). The percentage lysis for the different effector cell/target cell ratios is shown for days 1, 3, 6, 9, 15, 18 and 21 of the injection.

FIG. 4: effect of ETF on NK cells in vitro. The figure shows the percentage lysis as a function of the effector cell/target cell ratio for different doses of ETF.

FIG. 7: effect of ETF, when administered by injection, on NK cells: kinetics of the response at 1, 3 and 8 days after administering 15 µg of ETF by the intraperitoneal route.

DETAILED DESCRIPTION

Figure 1A:
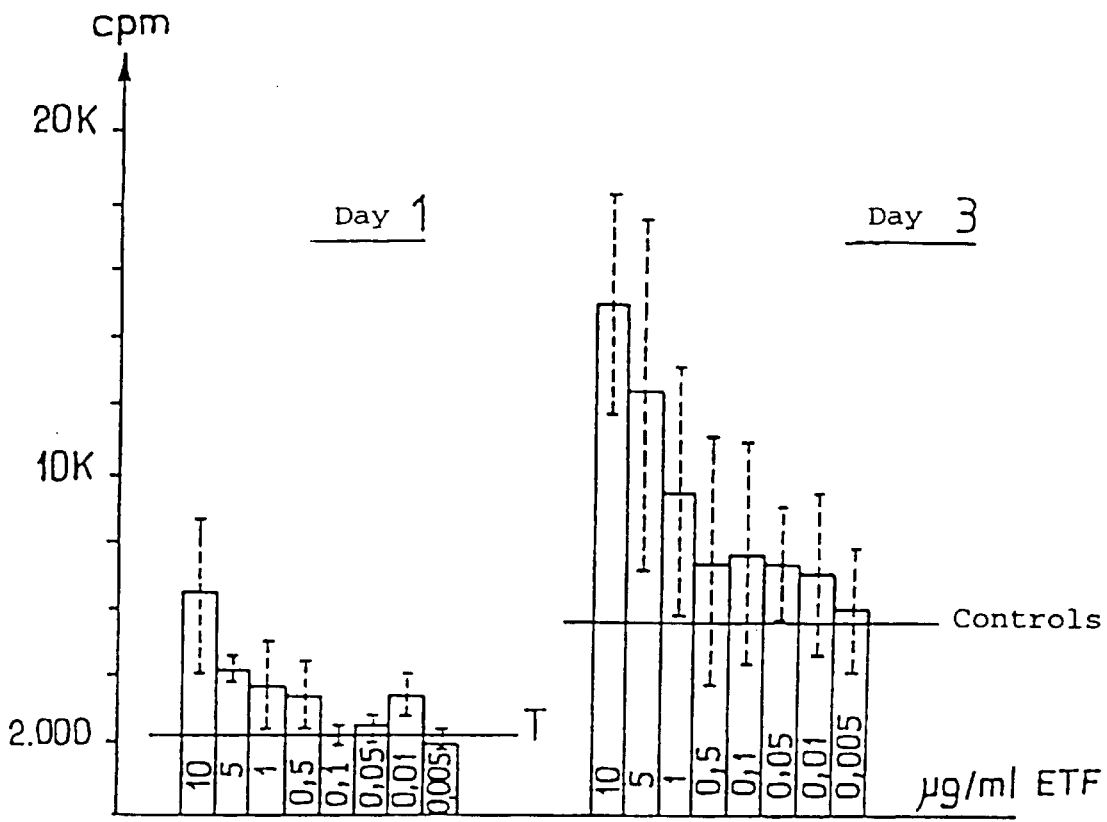
FIG. 1: effect of ETF on DNA synthesis.

The examples which follow are intended to illustrate the invention, in particular the immunostimulatory activity of the synthesized thymic peptides when administered by the topical route, without in any way limiting its scope.

EXAMPLE NO. 1

Preparation of Conjugate No. II
A-Pyr-Ala-Lys-Ser-Gln-Gly-Gly-Ser-NH$_2$ (SEQ ID NO: 6)
A=DL-lipoic acid The conjugate is synthesized in accordance with the following steps using described general methodology:
1—Boc-Gln-Gly-Gly-OMe
2—Trifluoroacetate-Gln-Gly-Gly-OMe
3—Z-Ser-NH-NH$_2$(But)→Bop→DIEA→DMF
4—Z-Ser-Glu-Gly-Gly-Ser-NH$_2$ (SEQ ID NO:12)
5—Lipoic acid→BOP→DIEA→DMF
6—Lipoyl-Pyr-Ala-Lys-Ser-Gln-Gly-Gly-Ser-NH$_2$ (SEQ ID NO:6)
HPLC analysis of the amino acids
Asp-1.02; Ser-1.77; Glu-1.0; Gly-2.00; Ala-0.91.

EXAMPLE NO. 2

Preparation of Conjugate No. III

A-Ala-Lys-Ser-Gln-Gly-Gly-Ser-Asn-NH$_2$ (SEQ ID NO:26)

A=adipic acid

The conjugate is synthesized in accordance with the following steps using general methodology:

1—Z-D-Ala-Lys-(Boc)-Ser(But)→DMF
2—Lys-(Boc)-Ser(But)-Gln(Mbh)→DMF
3—Gly-Gly-Ser(But)-Asn-O-But (SEQ NO:27)
4—Me.OH→CH$_3$COOH→D-Ala-Lys(Boc)-Ser(But)-Gln (Mbh) (SEQ ID NO:28)→Gly-Gly-Ser-Asn(But) (SEQ ID NO:29)
5—Adipic acid→BOP→DIEA
6—Adipoyl-Ala-Lys-Ser-Gln-Gly-Gly-Ser-Asn-NH$_2$ (SEQ ID NO:26)

HPLC analysis of the amino acids

Asp-1.02; Ser-1.77; Glu-1.0; Gly-2.00; Ala-0.91.

EXAMPLE NO. 3

Preparation of Conjugate No. I

A-Pyr-Ala-Lys-Ser-Gln-Gly-Gly-Ser-Asn-NH$_2$ (SEQ ID NO:5)

A=acetic acid

The methodology described in Example 1 is used to obtain this conjugate from the derivative: Ala-Lys(Boc)-Ser(But)-Gln-(Mbh)-Gly-Gly-Ser(But)-Asn(But) (SEQ ID NO:30) as previously described.

A homogenous product is obtained by chromatography at pH 2.3 in solvents G and H.

HPLC analysis of the amino acids.

Asp-0.97; Ser-1.67; Glu-1.84; Gly-2.00; Ala-0.98.

EXAMPLE 4

Measurement of Activity on IA+Langerhans Cells and THY.1.2+ Thymocytes of the Epidermis of C57-BL/6 Mice I Summary Keratinocytes of "C57-BL/6" mice which are stimulated with the peptide derivatives of the thymic hormones release mediators (cell messengers), such as ETAF, IL1 and IL6, which induce activation of the immune response of the immunocompetent cells of the epidermis, i.e. the Ia+Langerhans cells and the Thy 1.2+ thymocytes.

The measurement of this activation using immunofluorescence techniques is characteristic for the immunomodulatory activity of the thymic peptides.

II Materials and Methods

1—Experimental Samples—Code: ETF

In solution in propylene glycol at a concentration of $10^{-5}$ M/ml

ETF—peptide—No. I
ETF—peptide—No. III
ETF—peptide—No. XV
ETF—peptide—No. XIX
control=propylene glycol 2—Methodology 5 to 7-week-old male C 57-BL/6 mice, which are divided into groups of 4 per cage, and which have free access to water and food and which are subjected to a photoperiod of 12 h of light per 24 hours, are given a topical application of the peptide in propylene glycol (50 µl vol) on the dorsal surface of the ear daily for 5 consecutive days.

The animals are sacrificed on day 6. The ears are removed, with the dorsal and ventral surfaces being separated.

The tissues of the dorsal surface are immersed in Na EDTA (0.020 M) at 37° C. for 2 h.

After incubation, the epidermis is removed in the form of an intact sheet, fixed with acetone and rehydrated in PBS (phosphate buffer).

The Thy 1–2+ and Ia+ EDC (epidermal dendritic cells) are identified by indirect immunofluorescence double labeling.

In the case of each epidermal sheet, the number of cells per mm$^2$ is determined using the peripheral regions of the same surface.

The EDC (epidermal dendritic cells) carrying the Ia+ marker were identified using an anti-Ia+ monoclonal antibody.

The epidermal sheets are fixed with acetone and then incubated, at 37° C. for 1 h, in the presence of the anti-Ia+ monoclonal antibody, which has been labeled by the indirect immunoperoxidase method (Kit).

After having been incubated at 37° C. for 10 minutes with a solution of aminoethylcarbazole, the preparation is washed with PBS.

The Thy 1.2+ EDC were identified by indirect immunofluorescence double labeling. The epidermal sheets were fixed with acetone and then rehydrated in PBS.

The tissues were labeled simultaneously, at 4° C. for 16 h, with mouse anti-Thy 1.2+ antibody which was diluted 1:100. The tissue samples were washed three times in PBS for 60 min and then incubated, at 37° C. for 60 min, either with goat antimouse antibody which was coupled to rhodamine and diluted 1:20, or with goat antirabbit antibody which was coupled to fluorescein (fluorescine and diluted 1:20 in PBS. The tissues were then washed in PBS before being mounted as previously described.

The controls comprised epidermal sheets which were not labeled with primary antibody and which were incubated only in the presence of the secondary reagents in order to demonstrate any possible crossreactions with the antibodies which were conjugated to rhodamine and to fluorescein.

In the case of each epidermal sheet, the number of Ia+ Langerhans cells or Thy 1.2+ EDCs per square millimeter was determined by means of immunofluorescence, using a confocal Zeiss microscope which was equipped for this purpose, in four peripheral areas of the same surface. At least four animals were studied in each of the groups. The density of Ia+ Langerhans cells and Thy 1.2+ EDCs is shown for each measurement.

3—Results

The results summarized in Table I show that, when administered to C 57 BL/6 mice by the topical route, ETF and its homologs increase the activity of the resident cells of the cutaneous immune system in a highly significant manner.

In particular, a significant increase is seen, at doses of from 0.1 to 1 nanogram, in the phenotypes of the Ia+— (HLADR) Langerhans epidermal dendritic cells.

In parallel, a significant increase is also observed, at identical doses, in the activity of the epidermal thymocytes of the Thy 1.2+ phenotype, i.e. ETAF-dependent thymocytes.

The cutaneous immune response is dependent on the activity of the nucleated keratinocytes which secrete ETAF and the mediators of immunity, that is the 2nd signal without which there is no normal physiological immune function (L.D.H. immunodermatology). ETF and its homologs can be regarded as reestablishing the immune functions of the epidermis by activating the keratinocytes of the basal layers in a physiological manner, as opposed to exogenous antigenic stimulation.

Results expressed on 4 batches of 4 C 57 BL/6 mice
Number of Thy 1.2+ and Ia+ cells per mm² of epidermis

| Samples | Doses Nanog. | Thy 1.2+ cells 1 | 2 | 3 | 4 | Mean | % T | Ia+ cells 1 | 2 | 3 | 4 | Mean | % |
|---|---|---|---|---|---|---|---|---|---|---|---|---|---|
| PG controls | | 80 | 76 | 87 | 110 | 88.25 | | 98 | 102 | 100 | 110 | 102.50 | |
| ETF-I | 0.10 | 197 | 180 | 192 | 207 | 194.00 | 120 | 368 | 388 | 378 | 395 | 382.25 | 273 |
| | 0.50 | 200 | 208 | 199 | 219 | 206.50 | 134 | 360 | 392 | 386 | 399 | 384.25 | 275 |
| | 1.00 | 214 | 210 | 208 | 226 | 214.50 | 143 | 372 | 410 | 390 | 412 | 396.00 | 286 |
| ETF-III | 0.10 | 168 | 165 | 180 | 176 | 172.25 | 95 | 376 | 382 | 387 | 399 | 386.00 | 277 |
| | 0.50 | 190 | 190 | 205 | 200 | 196.25 | 122 | 380 | 388 | 299 | 388 | 363.75 | 255 |
| | 1.00 | 200 | 220 | 216 | 210 | 211.50 | 140 | 305 | 400 | 398 | 410 | 378.25 | 269 |
| ETF-XV | 0.10 | 160 | 158 | 160 | 170 | 162.00 | 84 | 315 | 326 | 320 | 330 | 322.75 | 215 |
| | 0.50 | 176 | 168 | 170 | 186 | 175.00 | 98 | 305 | 345 | 330 | 345 | 331.25 | 223 |
| | 1.00 | 198 | 180 | 188 | 199 | 191.25 | 117 | 348 | 360 | 348 | 350 | 351.50 | 243 |
| ETF-XIX | 0.10 | 216 | 210 | 219 | 212 | 214.25 | 143 | 360 | 390 | 378 | 320 | 362.00 | 253 |
| | 0.50 | 220 | 215 | 228 | 216 | 219.75 | 149 | 388 | 398 | 386 | 400 | 393.00 | 283 |
| | 1.00 | 227 | 238 | 230 | 225 | 230.00 | 161 | 400 | 410 | 438 | 415 | 415.75 | 306 |

EXAMPLE 5

Measurement of ETF No. IX Activity on Human Skin Keratinocytes Derived from Primary Culture I Materials and Methods 1—Cell Model Culture of normal human keratinocytes

| Sources: | Mammaplasty |
|---|---|
| Primary culture: | The tissues, which have been freshly biopsied under conditions of total asepsis, are digested in 0.25% trypsin, at +4° C., in order to separate the epidermis from the corium. |

The epidermis is then dissociated under gentle mechanical action, or enzymatically, in order to obtain the individual cells. Only the basal cells are capable of multiplying in vitro.

The culture is carried out at 37° C. in a controlled moist atmosphere (95% $o_2$—5% $CO_2$).

In monolayer culture, the calcium concentration is between 0.05 and 0.1 mM. Under these conditions, the keratinocytes proliferate rapidly but do not form strata. The synthesis of the keratinocytes is maintained. The intercellular spaces are wide: cell connections are maintained by microvillosities and not by tight junctions. While the tonofilaments of the perinuclear space can be seen, they are still not attached to the anchoring plaques.

Stratification can be induced by increasing the final calcium concentration in the culture medium to 1.2 mM. The formation of desmosomes then appears after 2 hours.

The level of intracellular potassium and sodium increases from the 12th hour onward; furthermore, it is not blocked by the usual $Ca^{2+}$/Na+ flux inhibitors.

Vertical stratification can be seen after 2 days, and cornified envelope cells complete their terminal differentiation.

2—Samples Analyzed

| I | ETF derivative No. IX, which has been lyophilized in Dextran (40 g/l) and which is at a concentration of $10^{-6}$ M in the final culture medium. |
|---|---|
| II | Crist. SIGMA thymopoietin - at a concentration of $10^{-6}$ M in the final culture medium. |
| III | Control: 15,000 D dextran - (40 g/l). |

-continued

| IV | Cell proteins - 50 micrograms per ml cell homogenate reference sol. |
|---|---|

3—Methodology

Human keratinocytes are cultured as described by Henning et al. (1983) or Fuchs et al. (1981). Air/liquid cultures are also carried out using the following methodology.

Collagen Lattices on Grids

Type I or type IV collagen is incorporated into the culture medium.

3T3 fibroblasts are added to this solution at a concentration of $1.5 \times 10^5$ /ml and seeded on 35 mm Petri dishes which are then placed at 37° C.

After the gel has been formed, medium is added so as to cover the lattices completely. The keratinocytes are seeded and maintained in submerged culture in this way for 7 days.

At this stage, the lattices are transferred onto stainless steel grids. These grids are placed in medium-containing dishes for from 7 to 24 days.

Artificial Basal Membrane

Bovine corneal endothelial cells are cultured on collagen-covered filters. After having been stimulated with a growth factor of the FGF type, these cells secrete collagen IV and laminin, and other molecules, which are deposited on the collagen, thereby reconstituting a basal pseudomembrane.

After the bovine endothelial cells have been removed, the keratinocytes are seeded on this support.

Artificial Corium

Fibroblasts are incorporated into a collagen gel. After retraction of the gel, the keratinocytes are seeded on this lattice.

Basal Membrane of the Corium

Fragments of human skin are de-epidermalized by being immersed at 37° C. for 5 days in PBS. After such a treatment, the epidermis detaches completely above the basal membrane. The fibroblasts are then killed by successive freezings and thawings. This tissue, which comprises the corium and the basal membrane, is then used as a nutrient layer for the keratinocytes.

| Culture on: | | Keratohyalin | 67 kD keratin |
|---|---|---|---|
| 1. Plastic + immersion | | − | − |
| 2. Filter covered with coll. I or IV | S E | − − | − − |
| 3. Filter covered with an artificial basal membrane | S E | − − | − − |
| 4. Artificial corium | S E | ± + | − ++ |
| 5. Natural corium which has been de-epidermalized and killed | S E | ± ++ | − ++ |

S = submerged
E = immersed

Differentiation of the epidermis is monitored by electron microscopy (Prunieras, 1988), by biochemical analysis (Tinois et al., 1993) and by immunological analysis (Woodcock et al., 1982, Prunieras, 1988). This latter analysis can make use of antiinvolucrin, antiepidermal transglutaminase, antifilaggrin and antikeratin (AE1, AE2 and AE3) antibodies.

The 48 Kd keratins are the markers of proliferation.

The 50 and 58 Kd keratins are the permanent keratin markers.

The 56.5 and 65/67 Kd keratins are the markers of differentiation.

The cell markers which are selected are the low-molecular-weight 46/47 KD keratins, which are specific for the growth and cell differentiation of the germinative cells.

The filaggrins are markers of keratohyalin.

Indirect fluorescent labeling by the sandwich technique—48 hours after adding calcium to the culture medium (stratification).

I—"SIGMA" Primary Antibodies
rat antihuman 46-47 KD keratin antibody
human antihuman 56.5/68 KD keratin antibody
human antikeratohyalin (filaggrin) antibody
II—"SIGMA" Secondary Antibodies
FITC-labeled mouse antirat Ig G2 antibody.
FITC-labeled goat antihuman Ig G antibody.
  Microscopic assays
  "confocal laser scanner Zeiss microscope"
  epifluorescent LSM 310
Use of immunofluorescence, with graphic recording, for measuring cell markers.
  Spectrofluorometric assays
  "Perkin Elmer LS-50 B spectrofluorimeter".
  on cell homogenate supernatants.
  Assays of cell proteins
  LOWRY technique using a Perkin Elmer UV spectrophotometer (cell homogenate supernatants).

II Results

Tables Nos. II and III summarize the effect of "ETF" peptide No. IX on the growth of the germinative cells of the basal and suprabasal layers of the epidermis—i.e. "young keratinocytes".

The fluorescence intensity of the cells treated with ETF No. IX is assessed in comparison with the fluorescence intensity of the controls.

A significant increase in the germinative prekeratinocyte cells, and their metabolic activity, is observed. In particular, structures resembling those of the thymus medulla are seen in relation to syntheses of low-molecular-weight keratin and "filaggrin" keratohyalins.

TABLE II

"Summary"
Effect of ETF on the synthesis by keratinocytes of 46–47 KD keratin and of cell proteins, as compared with a control (proteins expressed in micrograms/ml).

| Product | Concentration M | Keratin/ protein mean | Keratin/ protein standard deviation | Stimulation % |
|---|---|---|---|---|
| Thymopoietin | $10^{-6}$ | 94.8 | 3.4 | 19 |
| ETF No. IX | $10^{-6}$ | 151.5 | 14.9 | 90 |
| | $10^{-8}$ | 156.0 | 13.2 | 95 |
| | $10^{-10}$ | 148.9 | 22.9 | 86 |
| | $10^{-12}$ | 113.0 | 5.6 | 41 |

TABLE III

"Summary"
Effect of ETF on the synthesis by keratinocytes of keratohyalin and of proteins as compared with a control (proteins expressed in micrograms/ml).

| Product | Concentration M | Keratin/ protein mean | Keratin/ protein standard deviation | Stimulation % |
|---|---|---|---|---|
| Thymopoietin | $10^{-6}$ | 4.99 | 0.54 | 35 |
| ETF No. IX | $10^{-6}$ | 5.97 | 0.12 | 62 |
| | $10^{-8}$ | 6.75 | 0.66 | 83 |
| | $10^{-10}$ | 5.13 | 0.25 | 39 |
| | $10^{-12}$ | 5.11 | 0.39 | 38 |

EXAMPLE NO. 6

Effect of ETF on "Mononuclear Phagocyte System" Granulocytes

I Introduction

The immune response of the epidermis is dependent on the keratinocytes and the Langerhans cells, in association with other "granulocyte-thymocyte" cell lines, etc.

The Langerhans cells are considerably less capable of carrying out phagocytosis than are the keratinocytes, a fact which formally differentiates them from macrophages.

Phenotypically and functionally, they resemble the veiled cells of the afferent lymph and the interdigitated cells of the lymphatic nodes.

The action of the Langerhans cells results from cellular cooperation, in particular with the "phagocyte" granulocytic cells under the dominance of the keratinocytes.

It was therefore of interest to assess the effect of ETF on the phagocytic activity of the polymorphonuclear granulocytes and related cell systems, in particular the NK cells (ENKAF, epidermal cell-derived natural killer activating factor).

II—Effect of ETF on Blood Granulocytes

1) Protocol

Human peripheral blood polymorphonuclear cells (neutrophil granulocytes), which are at a concentration of $10^6$ cells/ml, are preincubated at 37° C. for 20 mm before adding luminol and serum-opsonized zymosan particles.

The chemiluminescence is measured every 3 minutes after the latter reagent has been added. The results for each point represent the mean of 5 independent measurements. (Standard deviation less than 5% on average). Two systems are employed:

A. The inducing agent is ETF peptide No. I, which is present during the whole of the test.

Normal human peripheral blood granulocytes, which are enriched by being sedimented in dextran, and which are freed of erythrocytes by hypotonic lysis. The ETF is tested at concentrations of 10, 1 and 0.1 µg/ml.

B. The ETF inducing agent is removed by washing following preincubation and prior to adding chemiluminescent reagents.

Normal human peripheral blood granulocytes, which are purified by settling through dextran and by hypotonic lysis of the erythrocytes. ETF is incubated with the granulocytes at 37° C. for 20 min and then removed by washing before opsonized zymosan and luminol are added.

2—Results: (the values represent the mean of 5 measurements)

System A

| Treatment of the cells | Chemiluminescence values at: (mm) | | | | | | |
|---|---|---|---|---|---|---|---|
| | 3 | 6 | 9 | 12 | 15 | 18 | 21 |
| PBS | 22,966 | 77,598 | 140,423 | 178,951 | 198,063 | 191,781 | 188,531 |
| ETF 10 µg/ml | 79,358 | 140,100 | 170,947 | 183,578 | 174,710 | 160,718 | 137,798 |
| 1 µg/ml | 59,867 | 138,846 | 183,578 | 207,713 | 203,449 | 188,901 | 168,813 |
| 0.1 µg/ml | 29,205 | 86,761 | 143,463 | 176,924 | 193,589 | 188,573 | 179,449 |

System B

| Treatment of the cells | Chemiluminescence values at: (mm) | | | | |
|---|---|---|---|---|---|
| | 6 | 9 | 12 | 15 | 18 |
| PBS | 69,924 | 114,751 | 144,838 | 162,594 | 164,750 |
| ETF 10 µg/ml | 103,105 | 119,677 | 125,307 | 119,952 | 112,499 |
| 0.1 µg/ml | 100,532 | 124,819 | 134,788 | 129,950 | 133,707 |

3—Conclusions

A. At concentrations of 10 and 1 µg/ml, ETF has a considerable impact in potentiating the chemiluminescence right from the start.

B. Even after washing, ETF, at concentrations of 10 and 0.1 µg/ml, induces significant activation of the granulocytes.

EXAMPLE 7

Effect of ETF on DNA Synthesis

I—Protocol—Sample: ETF Peptide No. VII

A pool of normal mouse spleen cells is obtained and incubated with ETF alone, at increasing doses, in microtiter plates. The DNA is assayed on D1, D3 and D5.

Figure 1B:
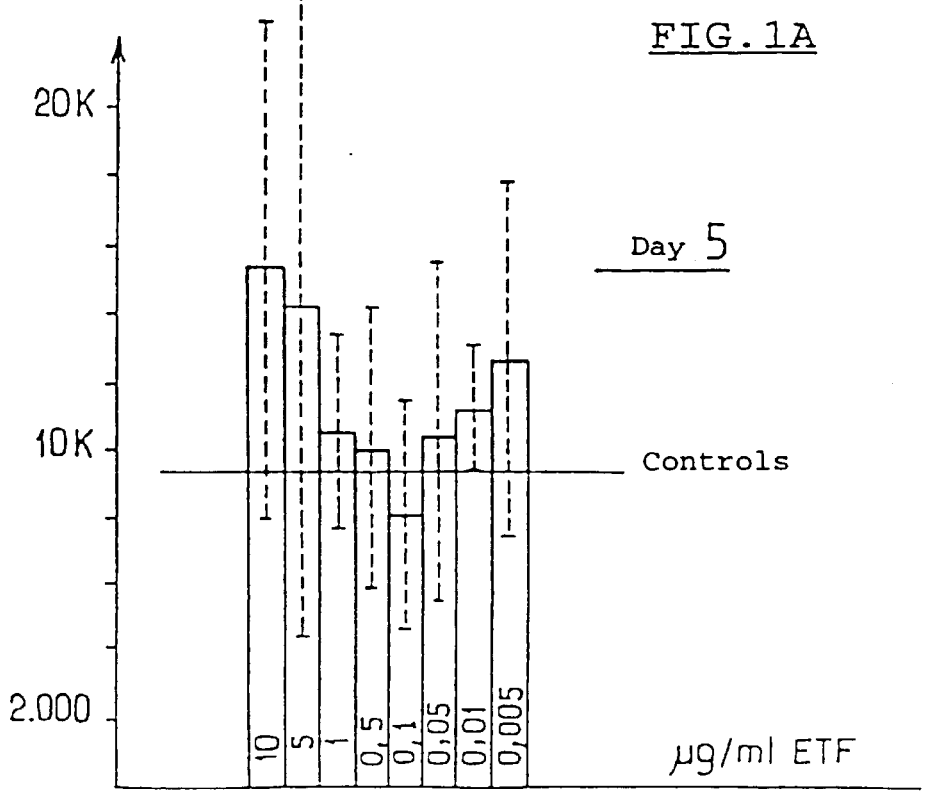

The results are presented in FIG. 1.

II Conclusions

The ETF shows a very clear response, which is proportional to the dose. The strongest dose employed (10 µg/ml) gives the greatest DNA synthesis on all the days of the control, with a maximum on day 3. It should be noted, however, that since the base values are higher on day 3, the specific response is perhaps in actual fact earlier.

EXAMPLE 8

Effect of ETF on Lysis Plaque-Forming Cells (PFC)

I Protocol

50 Balb/C mice which are being given 5 µg of ETF by the s.c. route. $10^8$ SRBC (sheep red blood corpuscles) in 0.1 ml of PBS are injected i.v. 20, 10 and 3 days after the ETF or 2 days before it. PFC technique of Cunningham and Szenberg.

II Results

Number of PFC per $10^6$ spleen cells.

| Treatment | Date of immuno-stimulation | Number of PFC at | | | |
|---|---|---|---|---|---|
| | | D + 3 | D + 4 | D + 5 | D + 6 |
| SRBC Control | 0 | 86 | 509 | 374 | 119 |
| 5 µg of ETF s.c. | D − 20 | 69 | 438 | 318 | 84 |
| | D − 10 | <u>323</u> | <u>823</u> | 337 | 104 |
| | D − 3 | 57 | 399 | 353 | 129 |
| | D + 2 | 119 | 410 | 336 | 135 |

III Conclusions

A response is observed which exhibits a maximum at D+4, with a very significant, substantial increase in the number of PFC in the animals which were given the ETF 10 days before the antigen.

EXAMPLE 9

Effect of ETF on NK Cells

I Effect of ETF on NK Cells—Topical Route

1—General Protocol for the Topical Route

CBA/H mice (90 mice) target cells:

YAC-1 cells which are sensitive to NK cells

P 815 cells which are not sensitive to NK cells

ETF No. VII

Each day for 14 consecutive days, the mice are given 15 µg of ETF, in the form of a $10^{-5}$ M/ml solution in propylene glycol, by the topical route. An identical booster dose is administered on day 18.

Lytic activity is measured every 3 days by counting the $^{51}$Cr which is released during 4 hours of incubation for effector cell:target cell ratios of 200:1, 100:1, 50:1 and 25:1.

Figure 3A:
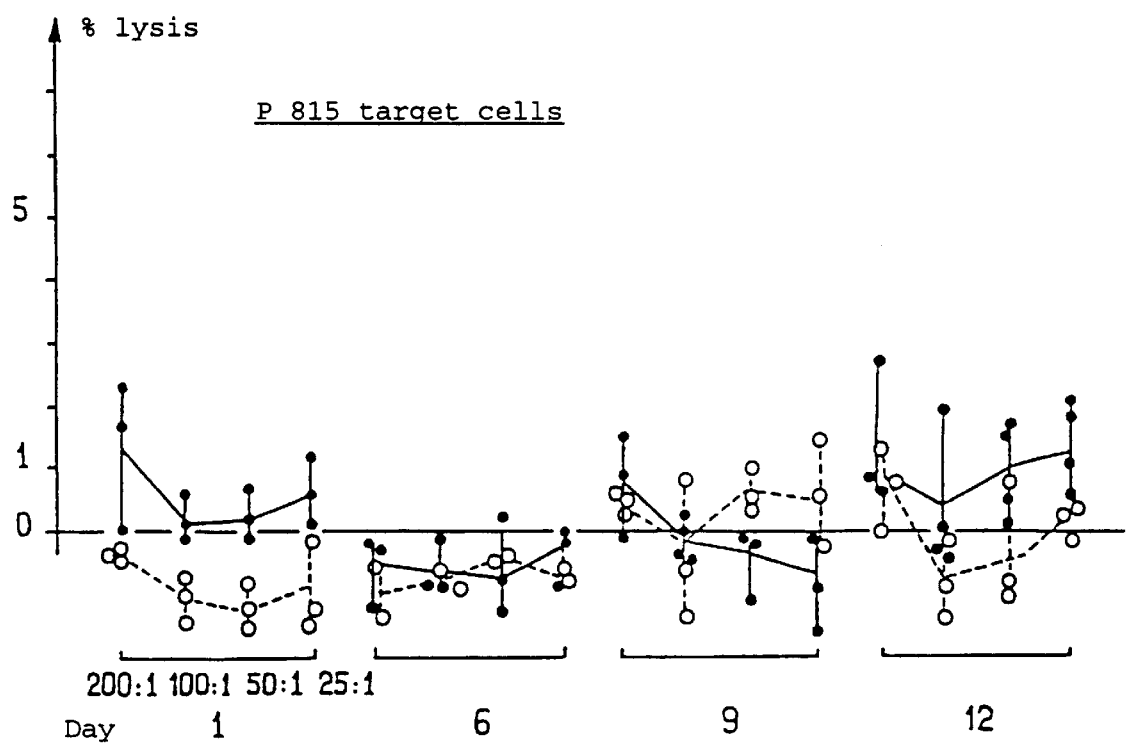
FIG. 3: effect of ETF, when administered by the topical route, on NK cells (target cells P815).
Figure 3B:
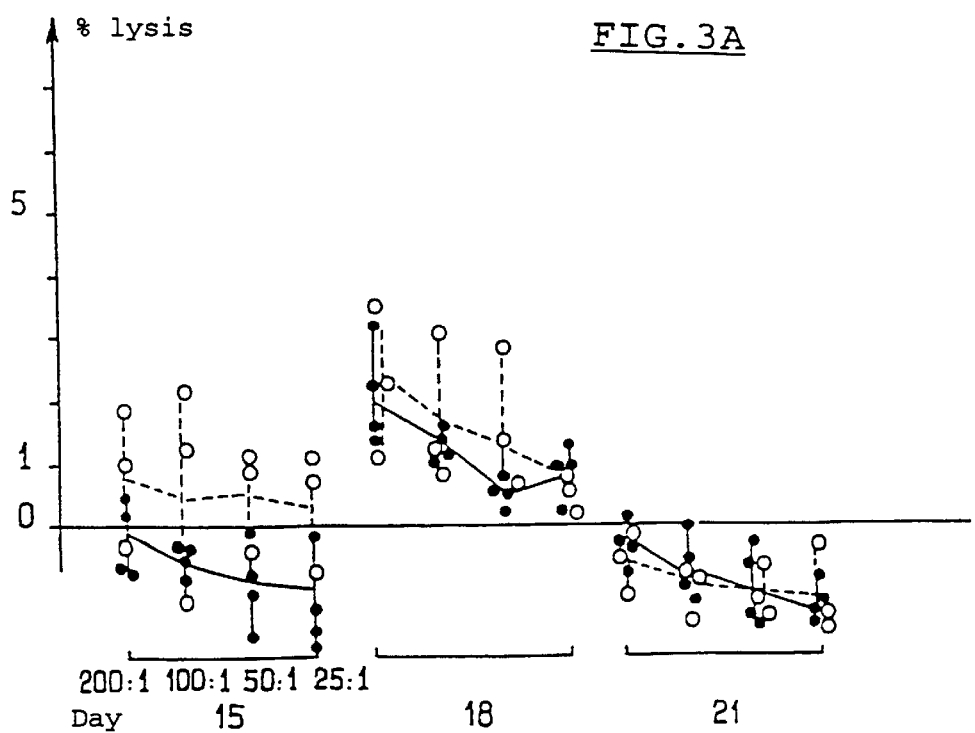

The results on NK cells, when the ETF is administered by the topical route, are presented in FIGS. 2 and 3.

The results are extremely clear. A highly significant increase in NK activity is observed, as a function of time, after beginning the treatment with ETF. This activity, which is discernible from day 3 onward, becomes very substantial on days 6 and 9 and is maintained at a very high level for the whole duration of the experiment (21 days).

2—Conclusions

Non-specific cytotoxicity on the P 815 cells is not detectable at any time during the experiment. This excludes the possibility that administration of the ETF might lead to the induction of non-specifically cytolytic cells or to the polyclonal activation of cytolytic T cells.

II Effect of ETF on NK Cells in vitro

1—"In-vitro" Assay Protocol

Normal CBA mouse spleen cells. Incubator at 37° C.+CO2. $10^7$ cells per ml of RPMI 1640 medium+5% fetal calf serum. Incubation with varying quantities of the substance to be studied. YAC-1 target cells.

Lysis is measured by counting the $^{51}$Cr which is released during 4 hours of incubation for effector cell/target cell ratios of 200:1, 100:1, 50:1 and 25:1.

The results are presented in FIG. 4.

2—Conclusions

ETF very strongly stimulates the activity of the NK cells in vitro in a manner which is proportional to the dose.

At a concentration of 0.1 µg/ml, the activity of ETF is still much greater than that of 25 µg of poly I:C/ml.

(Activity is at least 100 times greater than that of the reference product poly I:C, which is an interferon inducer).

III Effect of ETF on NK Cells—Injectable Route

1—General Protocol for an Injectable Route 4 to 5-month-old CBA/H mice. (140 mice) Target cells:

YAC-1 cells which are sensitive to NK cells (lymphoma induced/moloney virus)

P 815 cells which are insensitive to NK cells (DBA/2 mastocytoma)

The substance to be tested (ETF No. VII) is injected in 0.2 ml of PBS by the i.p. route 24 hours before the test. Lysis is measured by counting the 51 Cr which is released during 4 hours of incubation for effector cell/target cell ratios of 200:1, 100:1, 50:1 and 25:1.

2—NK Results/Injectable Route

Figure 5A:
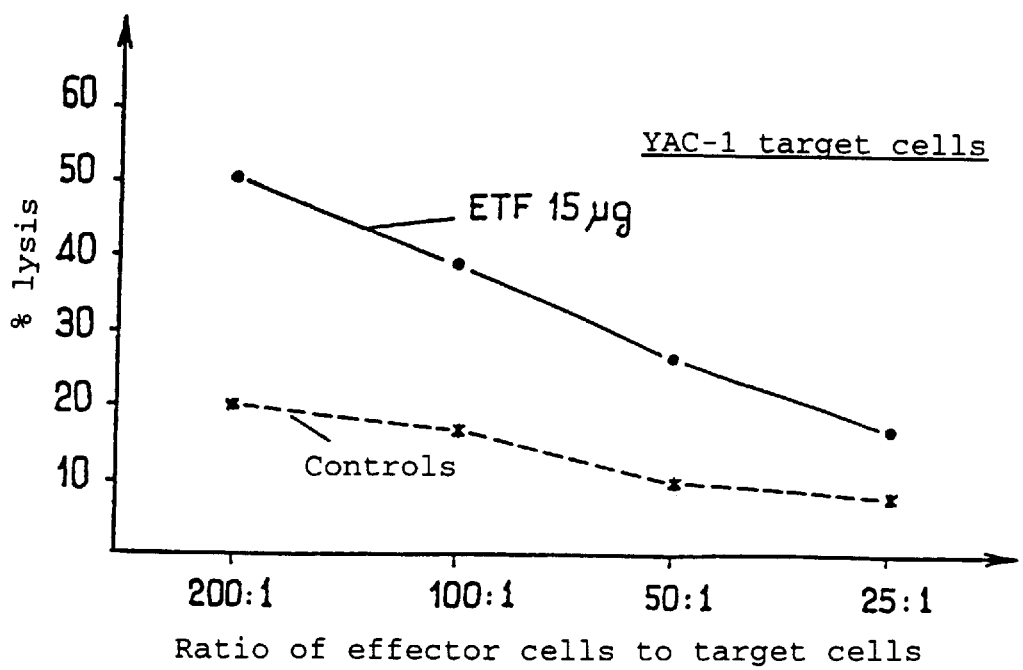
FIG. 5: effect of ETF, when administered by injection, on NK cells. Percentage lysis as a function of the effector cell/target cell ratio is shown both after stimulation with 15 µg of ETF and in the case of control animals.
Figure 5B:
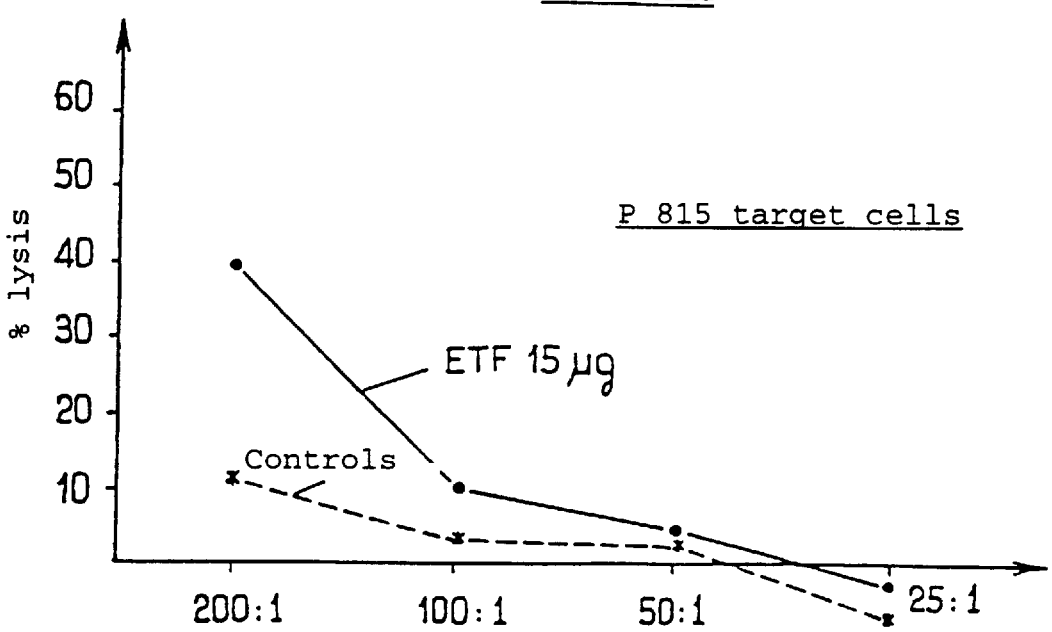

The results on the effect of the ETF in stimulating the NK cells are given in FIG. 5. They show strong activation, which is very significant ($P<0.01$), of the NK cells in the animals which were given the ETF (15 mg/i.p.) as compared with the controls. No non-specific cytotoxicity on the P815 cells was observed.

Figure 6A:
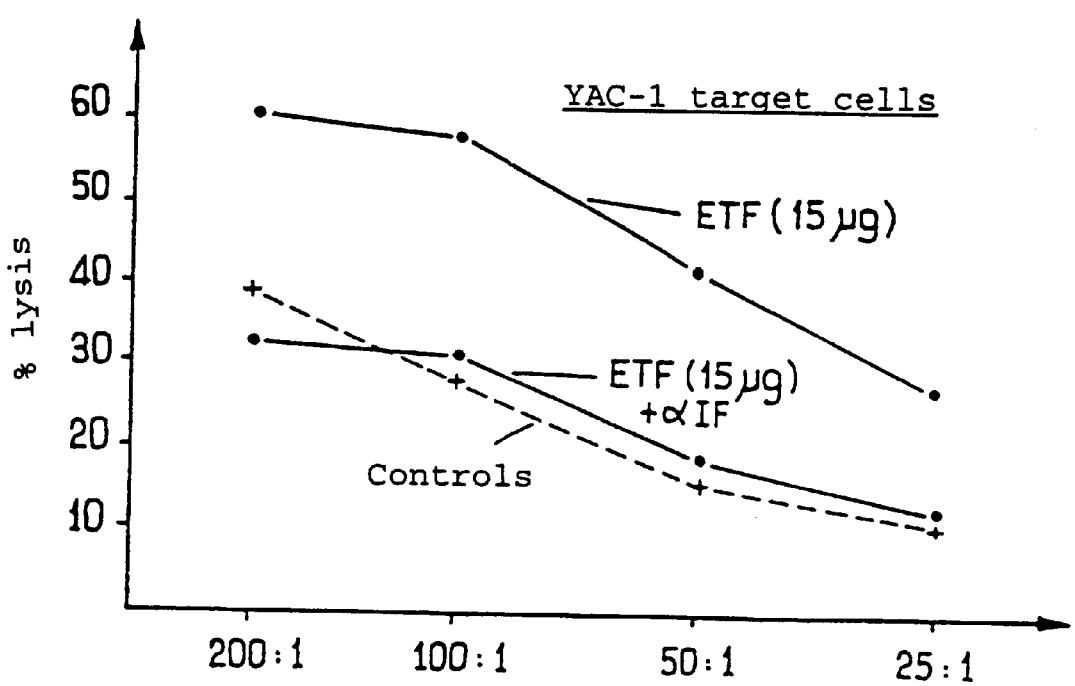
FIG. 6: role of interferon in stimulation of NK cells by ETF when administered by injection. The percentage lysis is given as a function of the effector cell/target cell ratio in the presence or absence of antiinterferon.
Figure 6B:
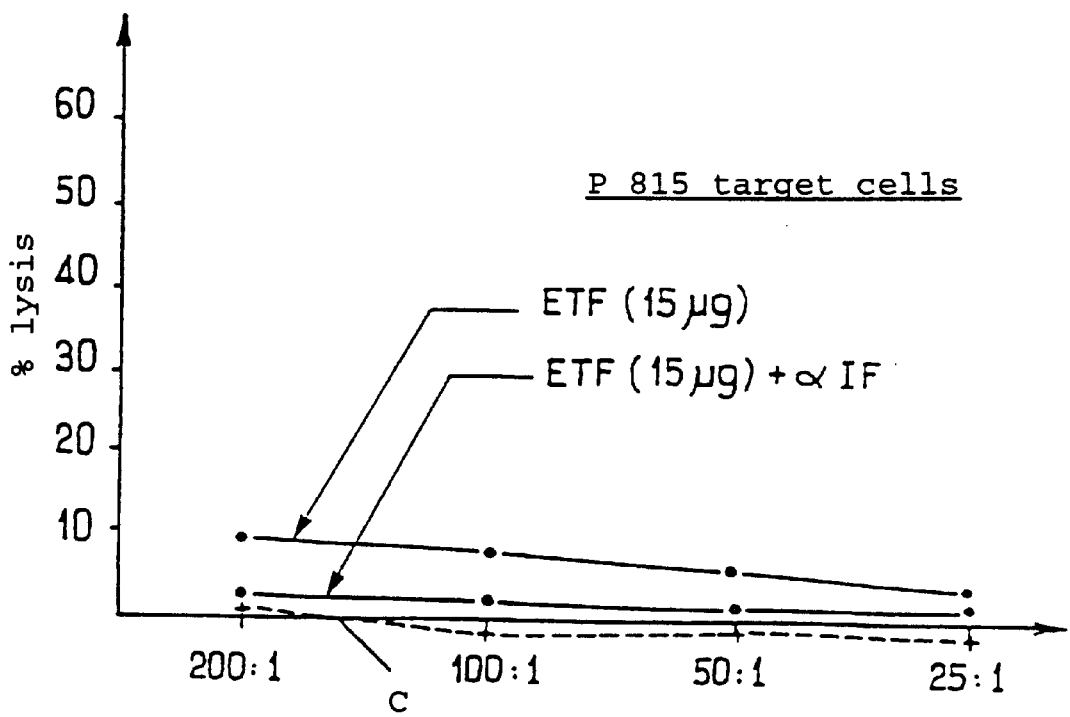

It can be seen from FIG. 6 that activation of the NK cells by ETF is due to an interferon induction effect. A drastic reduction in the NK cells is observed when antiinterferon ($\alpha$-IF) is administered simultaneously.

The kinetics of the response of the NK cells on days 1, 3 and 8 of the injection is shown, in comparison with a PBS control, in FIG. 7. When administration is by an injectable route, stimulation of the NK cells by ETF is of short duration.

At doses of tilorone of 1 mg per animal, ETF stimulates both NK cells and pre-NK cells identically in young animals (from 7 to 9 months).

Figure Legends

FIG. 1:

ETF. DNA synthesis

FIG. 2:

ETF. NK cells/topical route o---o    treated samples/ETF
•——•    control samples

FIG. 3:

ETF. NK cells/topical route

•——•    control samples
o---o    treated samples

FIG. 4:

ETF: NK cells 'in vitro'

Comparison of 0.1→100 µg of ETF/ml with 25 µg of poly I:C/ml o——o——    25 µg of Poly I:C/ml (+ control)
*——*——    PBS (- control)
•---•---    0.1 µg of ETF/ml
+---+---    1.0 µg of ETF/ml
□---□---    10.0 µg of ETF/ml
△---△---    100.0 µg of ETF/ml

FIG. 5:

ETF. NK cells, injectable route

FIG. 6:

ETF. NK cells, injectable route

Role of interferon in stimulating NK cells with ETF

FIG. 7:

ETF. NK cells, injectable route

Kinetics of the NK response to ETF

NK test on days 1, 3 and 8 following 15 µg of ETF by the i.p. route

BIBLIOGRAPHY

E. TINOIS, H. DUMAS, Q. GAETANI, D. DUPONT, X. POURADIER DUTEIL, A. ROUGIER Nouv. Dermatol. 12 No. 7, 510, 1993.

H. HENNING, K. A. HOLBROOK, S. H. YUSPA The J. of Invest. Dermatol. 81 50–55, 1983.

E. FUCHS, H. GREEN CELL, 25 617–625, 1981.

M. PRUNIERAS In-vitro methods in pharmacotoxicology, INSERM Symposium 170, 67–76, 1988.

J. WOODCOCK-MITCHELL, R. EICHNER, W. G. NELSON, T. SUN The J. of Cell Biol., 95 580–588, 1992.

What is claimed is:

1. A method of correcting deficiencies of the immune system in a host animal, comprising topically administering to the host animal a therapeutically effective amount of a composition, comprising:
   (i) at least one peptide conjugate which includes a sequence of at least 3 amino acids, which are derived from a thymic hormone selected from the group consisting of thymulin and thymopoietin, wherein said sequence is conjugated with at least one compound which is selected from the group consisting of:
   (A) monocarboxylic acids of the general formula

HOOC—R     (I)

in which R represents a straight-chain or branched, optionally substituted $C_1$–$C_{20}$ aliphatic radical, which can contain one or more unsaturations, or the alcohol, aldehyde, or amide derivatives of the acids of the formula I; and
   (B) dicarboxylic acids of the general formula

HOOC—$R_1$—COOH     (II)

in which $R_1$ represents a straight-chain or branched divalent aliphatic radical comprising at least 3 carbon atoms, which can contain one or more unsaturations and can optionally be substituted; and
   (ii) a pharmaceutically or cosmetologically acceptable excipient that is suitable for topical administration.

2. The method according to claim 1, wherein the composition is in an amount effective to increase proliferation of cells of the cutaneous immune system.

3. The method according to claim 1, wherein the composition is in an amount effective to stimulate growth of germinative cells of the basal or suprabasal layers of the epidermis.

4. The method according to claim 1, wherein R represents:
   (A) a monounsaturated radical having the cis or trans configuration, of the general formula $R_2$—CH=CH— in which $R_2$ represents a straight-chain or branched alkyl radical comprising at least 6 carbon atoms, which is optionally substituted by an amino, hydroxyl or oxo group; or
   (B) a substituted or unsubstituted, straight-chain or branched $C_{1-C20}$ aliphatic radical, which can contain one or more unsaturations and which can be substituted by one or more radicals which are selected from the group consisting of $NH_2$, OH, oxo, thiol, and a non-aromatic cyclic radical which contains from 5 to 6 atoms in the cycle, 1 or 2 of which can be different from carbon.

5. The method according to claim 1, wherein $R_1$ represents an optionally substituted $C_4$–$C_8$ alkylene radical.

6. The method according to claim 1, wherein the acids of the general formula I or II are selected from the group consisting of acetic acid and its derivatives, pyroglutamic acid, DL-lipoic acid and its derivatives, dihydrolipoic acid and derivatives, N-lipoyllysine, adipic acid, α-aminoadipic acid, pimelic acid, sebacic acid and derivatives, and the α-monounsaturated fatty acids in which $R_2$ represents a straight-chain or branched C7 alkyl radical.

7. The method according to claim 6, wherein the acids of the general formula I or II are selected from the group consisting of acetic acid and its derivatives, pyroglutamic acid, DL-lipoic acid and its derivatives, dihydrolipoic acid, N-lipoyllysine acid, adipic acid, α-aminoadipic acid, pimelic acid, sebacic acid and its derivatives, trans-10-hydroxy-Δ2-decenoic acid, and trans-9-oxodecenoic acid.

8. The method according to claim 1, wherein the amino acid sequence is linked to the acid or to the derivative of the formula I or II in salt, ester, or amide form.

9. The method according to claim 1, wherein the conjugate has the general formula A[X-Gln-Gly-Gly-Y] (SEQ ID NO: 1)     (III)

in which:
   (i) A is a compound of the general formula I or II or the corresponding radical;
   (ii) X is selected from the group consisting of: Ser, Lys-Ser, Ala-Lys-Ser, Pyr-Ala-Lys-Ser (SEQ ID NO: 2), a bond, and Glx-Ala-Lys-Ser (SEQ ID NO: 3), in which Glx is: Pyr-Glu, Glu, or Gly and its derivatives; and
   (iii) Y is selected from the group consisting of: Ser-Asn-OH, Ser-Asn-NH2, Ser-OH, and Ser-NH2;
and wherein the amino acids are in the D, L, or DL form.

10. The method according to claim 1, wherein the conjugate has the general formula A[W-Lys-Asp-Z] (SEQ ID NO: 15)     (IV)

in which
   (i) A is a compound of the general formula I or II or the corresponding radical;
   (ii) W is selected from the group consisting of: Glu-Gln-Arg, Gln-Arg, Arg, Arg-Lys-, Arg-Lys-Asp, and a bond; and
   (iii) Z is selected from the group consisting of: Val-Tyr-$NH_2$, Val-Tyr-OH, Val-$NH_2$, Val-OH, Tyr-OH, Tyr-$NH_2$, OH, and $NH_2$,
wherein at least one of the sequences is Arg-Lys-Asp or Lys-Asp-Val and wherein the amino acids are in the D, L, or DL form.

11. The method according to claim 1, wherein the conjugate is selected from the group consisting of:
I  A-Pyr-Ala-Lys-Ser-Gln-Gly-Gly-Ser-Asn-$NH_2$ (SEQ ID NO: 5);
II  A-Pyr-Ala-Lys-Ser-Gln-Gly-Gly-Ser-$NH_2$ (SEQ ID NO: 6);
III  A-Ala-Lys-Ser-Gln-Gly-Gly-Ser-Asn-$NH_2$ (SEQ ID NO: 7);
IV  A-Ala-Lys-Ser-Gln-Gly-Gly-Ser-$NH_2$ (SEQ ID NO: 8);
V  A-Lys-Ser-Gln-Gly-Gly-Ser-Asn-$NH_2$ (SEQ ID NO: 9);
VI  A-Lys-Ser-Gln-Gly-Gly-Ser-$NH_2$ (SEQ ID NO: 10);
VII  A-Ser-Gln-Gly-Gly-Ser-Asn-$NH_2$ (SEQ ID NO: 11);
VIII  A-Ser-Gln-Gly-Gly-Ser-$NH_2$ (SEQ ID NO: 12);
IX  A-Gln-Gly-Gly-Ser-Asn-$NH_2$ (SEQ ID NO: 13);
X  A-Gln-Gly-Gly-Ser-$NH_2$ (SEQ ID NO: 4);
XI  A-Glu-Gln-Arg-Lys-Asp-Val-Tyr-$NH_2$ (SEQ ID NO: 17);
XII  A-Glu-Gln-Arg-Lys-Asp-Val-Tyr-OH (SEQ ID NO: 17);
XIII A-Gln-Arg-Lys-Asp-Val-Tyr-$NH_2$ (SEQ ID NO: 18);
XIV A-Gln-Arg-Lys-Asp-Val-Tyr-OH (SEQ ID NO: 18);
XV  A-Arg-Lys-Asp-Val-Tyr-$NH_2$ (SEQ ID NO: 19);
XVI A-Arg-Lys-Asp-Val-Tyr-OH (SEQ ID NO: 19);
XVII A-Lys-Asp-Val-Tyr-$NH_2$ (SEQ ID NO: 20);

XVIII A-Lys-Asp-Val-Tyr-OH (SEQ ID NO: 20);
XIX A-Arg-Lys-Asp-Val-NH$_2$ (SEQ ID NO: 21);
XX A-Arg-Lys-Asp-Val-OH (SEQ ID NO: 21);
XXI A-Arg-Lys-Asp-NH$_2$ (SEQ ID NO: 26);
XXII A-Arg-Lys-Asp-OH; and
XXIII A-Ala-Lys-Ser-Gln-Gly-Gly-Ser-Asn-OH (SEQ ID NO:14), wherein A is a compound of the formula I or II or the corresponding radical.

12. The method according to claim 1, wherein at least one amino acid of the amino acid sequence is glycosylated.

13. The method according to claim 1, wherein at least one conjugate is a metallopeptide complex linked chemically or physically to a zinc salt.

14. The method according to claim 1, wherein the conjugate is selected from the group consisting of acetic acid-Arg-Lys-Asp-Val-Tyr-NH$_2$ (SEQ ID NO:19); and Pyr-Ala-Lys-Ser-Gln-Gly-Gly-Ser-Asn-OH (SEQ ID NO:25).

15. The method according to claim 1, wherein the amino acids are independently in D, L, or DL form.

16. The method according to claim 1, wherein the aliphatic radical of R$_1$ has 3 to 10 carbon atoms.

17. The method according to claim 16, wherein the aliphatic radical of R$_1$ is selected from the group consisting of alkylene, alkenylene, and alkynylene.

18. The method according to claim 1, wherein the aliphatic radical of R$_1$ is substituted by one or more amino, hydroxyl, or oxo groups or by a C$_1$–C$_3$ alkyl radical.

19. The method according to claim 1, wherein the aliphatic radical of R$_1$ forms a cycle with one of the acid functions.

20. The method according to claim 4, wherein the alkyl radical of R$_2$ has from 6 to 16 carbon atoms.

21. The method according to claim 4, wherein the aliphatic radical is selected from the group consisting of alkyl, alkenyl, and alkynyl.

22. The method according to claim 4, wherein wherein the atoms in the cycle other than carbon are selected from the group consisting of S, O, and N.

23. The method according to claim 4, wherein the cycle is substituted with C$_1$ to C$_3$ alkyl radicals.

24. The method according to claim 23, wherein the substituted alkyl radical is methyl.

25. the method according to claim 6, wherein R$_2$ represents hydroxydecenoic acid or decenoilic acid.

26. The method according to claim 11, wherein the amino acids are in the D, L, or DL form.

27. The method according to claims 1, 9, or 10, wherein the excipient is propylene glycol.

28. The method according to claim 7, wherein the acids of general formula I or II are selected from the group consisting of acetic acid and its derivatives, DL-lipoic acid and its derivatives, and adipic acid.

* * * * *

SEQUENCE LISTING

<160> NUMBER OF SEQ ID NOS: 30

<210> SEQ ID NO 1
<211> LENGTH: 9
<212> TYPE: PRT
<213> ORGANISM: Artificial Sequence
<220> FEATURE:
<223> OTHER INFORMATION: Description of Artificial Sequence: synthetic
      peptide derived from thymic hormones
<223> OTHER INFORMATION: Xaa at positions 1-4, in the peptide's largest
      embodiment, may be pyro-glu-ala-lys-ser,
      glu-ala-lys-ser or gly-ala-lys-ser; the peptide
      may also encompass smaller embodiments
<223> OTHER INFORMATION: Xaa at position 8-9, in the peptide's largest
      embodiment, is ser-asn; the peptide may also
      encompass smaller embodiments consisting of
      only ser.

<400> SEQUENCE: 1

Xaa Xaa Xaa Xaa Gln Gly Gly Xaa Xaa
 1               5

<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence: synthetic
      peptide derived from thymic hormones
<223> OTHER INFORMATION: Xaa at position 1 is pyro-glu.

<400> SEQUENCE: 2

Xaa Ala Lys Ser
 1

<210> SEQ ID NO 3
<211> LENGTH: 4
<212> TYPE: PRT
<213> ORGANISM: Artificial Sequence
<220> FEATURE:
<223> OTHER INFORMATION: Description of Artificial Sequence: synthetic
      peptide derived from thymic hormones
<223> OTHER INFORMATION: Xaa at position 1 is pyro-glu, glu or gly.

<400> SEQUENCE: 3

Xaa Ala Lys Ser
 1

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence: synthetic
      peptide derived from thymic hormones

<400> SEQUENCE: 4

Gln Gly Gly Ser
 1

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: synthetic
      peptide derived from thymic hormones
<223> OTHER INFORMATION: Xaa at position 1 is pyro-glu.

```
<400> SEQUENCE: 5

Xaa Ala Lys Ser Gln Gly Gly Ser Asn
 1               5

<210> SEQ ID NO 6
<211> LENGTH: 8
<212> TYPE: PRT
<213> ORGANISM: Artificial Sequence
<220> FEATURE:
<223> OTHER INFORMATION: Description of Artificial Sequence: synthetic
      peptide derived from thymic hormones
<223> OTHER INFORMATION: Xaa at position 1 is pyro-glu.

<400> SEQUENCE: 6

Xaa Ala Lys Ser Gln Gly Gly Ser
 1               5

<210> SEQ ID NO 7
<211> LENGTH: 8
<212> TYPE: PRT
<213> ORGANISM: Artificial Sequence
<220> FEATURE:
<223> OTHER INFORMATION: Description of Artificial Sequence: synthetic
      peptide derived from thymic hormones

<400> SEQUENCE: 7

Ala Lys Ser Gln Gly Gly Ser Asn
 1               5

<210> SEQ ID NO 8
<211> LENGTH: 7
<212> TYPE: PRT
<213> ORGANISM: Artificial Sequence
<220> FEATURE:
<223> OTHER INFORMATION: Description of Artificial Sequence: synthetic
      peptide derived from thymic hormones

<400> SEQUENCE: 8

Ala Lys Ser Gln Gly Gly Ser
 1               5

<210> SEQ ID NO 9
<211> LENGTH: 7
<212> TYPE: PRT
<213> ORGANISM: Artificial Sequence
<220> FEATURE:
<223> OTHER INFORMATION: Description of Artificial Sequence: synthetic
      peptide derived from thymic hormones

<400> SEQUENCE: 9

Lys Ser Gln Gly Gly Ser Asn
 1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence: synthetic
      peptide derived from thymic hormones

<400> SEQUENCE: 10

Lys Ser Gln Gly Gly Ser
 1               5

<210> SEQ ID NO 11
```

```
<211> LENGTH: 6
<212> TYPE: PRT
<213> ORGANISM: Artificial Sequence
<220> FEATURE:
<223> OTHER INFORMATION: Description of Artificial Sequence: synthetic
      peptide derived from thymic hormones

<400> SEQUENCE: 11

Ser Gln Gly Gly Ser Asn
 1               5

<210> SEQ ID NO 12
<211> LENGTH: 5
<212> TYPE: PRT
<213> ORGANISM: Artificial Sequence
<220> FEATURE:
<223> OTHER INFORMATION: Description of Artificial Sequence: synthetic
      peptide derived from thymic hormones

<400> SEQUENCE: 12

Ser Gln Gly Gly Ser
 1               5

<210> SEQ ID NO 13
<211> LENGTH: 5
<212> TYPE: PRT
<213> ORGANISM: Artificial Sequence
<220> FEATURE:
<223> OTHER INFORMATION: Description of Artificial Sequence: synthetic
      peptide derived from thymic hormones

<400> SEQUENCE: 13

Gln Gly Gly Ser Asn
 1               5

<210> SEQ ID NO 14
<211> LENGTH: 8
<212> TYPE: PRT
<213> ORGANISM: Artificial Sequence
<220> FEATURE:
<223> OTHER INFORMATION: Description of Artificial Sequence: synthetic
      peptide derived from thymic hormones

<400> SEQUENCE: 14

Ala Lys Ser Gln Gly Gly Ser Asn
 1               5

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: synthetic
      peptide derived from thymic hormones
<223> OTHER INFORMATION: Xaa at positions 1-3, in the peptide's largest
      embodiment, may be glu-gln-arg or arg-lys-asp; the
      peptide may also encompass smaller embodiments
      consisting of gln-arg, arg-lys or arg.
<223> OTHER INFORMATION: Xaa at positions 6-7, in the peptide's largest
      embodiment, are val-tyr; the peptide may also
      encompass smaller embodiments consisting of
      only val or tyr.

<400> SEQUENCE: 15

Xaa Xaa Xaa Lys Asp Xaa Xaa
 1               5

<210> SEQ ID NO 16
<211> LENGTH: 4
```

```
<212> TYPE: PRT
<213> ORGANISM: Artificial Sequence
<220> FEATURE:
<223> OTHER INFORMATION: Description of Artificial Sequence: synthetic
      peptide derived from thymic hormones

<400> SEQUENCE: 16

Arg Lys Asp Val
  1

<210> SEQ ID NO 17
<211> LENGTH: 7
<212> TYPE: PRT
<213> ORGANISM: Artificial Sequence
<220> FEATURE:
<223> OTHER INFORMATION: Description of Artificial Sequence: synthetic
      peptide derived from thymic hormones
<223> OTHER INFORMATION: this peptide may have an OH or NH2 c-terminus.

<400> SEQUENCE: 17

Glu Gln Arg Lys Asp Val Tyr
  1               5

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: synthetic
      peptide derived from thymic hormones
<223> OTHER INFORMATION: this peptide may have an OH or NH2 c-terminus.

<400> SEQUENCE: 18

Gln Arg Lys Asp Val Tyr
  1               5

<210> SEQ ID NO 19
<211> LENGTH: 5
<212> TYPE: PRT
<213> ORGANISM: Artificial Sequence
<220> FEATURE:
<223> OTHER INFORMATION: Description of Artificial Sequence: synthetic
      peptide derived from thymic hormones
<223> OTHER INFORMATION: this peptide may have an OH or NH2 c-terminus.

<400> SEQUENCE: 19

Arg Lys Asp Val Tyr
  1               5

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence: synthetic
      peptide derived from thymic hormones
<223> OTHER INFORMATION: this peptide may have an OH or NH2 c-terminus.

<400> SEQUENCE: 20

Lys Asp Val Tyr
  1

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: synthetic
      peptide derived from thymic hormones
```

```
<223> OTHER INFORMATION: this peptide may have an OH or NH2 c-terminus.

<400> SEQUENCE: 21

Arg Lys Asp Val
 1

<210> SEQ ID NO 22
<211> LENGTH: 5
<212> TYPE: PRT
<213> ORGANISM: Artificial Sequence
<220> FEATURE:
<223> OTHER INFORMATION: Description of Artificial Sequence: synthetic
      peptide derived from thymic hormones

<400> SEQUENCE: 22

Ala Lys Gln Gly Gly
 1               5

<210> SEQ ID NO 23
<211> LENGTH: 8
<212> TYPE: PRT
<213> ORGANISM: Artificial Sequence
<220> FEATURE:
<223> OTHER INFORMATION: Description of Artificial Sequence: synthetic
      peptide derived from thymic hormones
<223> OTHER INFORMATION: Xaa at positions 1-3, in the peptide's largest
      embodiment, are ala-lys-ser; the peptide may
      also encompass a smaller embodiment consisting
      of only ser.

<400> SEQUENCE: 23

Xaa Xaa Xaa Gln Gly Gly Ser Asn
 1               5

<210> SEQ ID NO 24
<211> LENGTH: 8
<212> TYPE: PRT
<213> ORGANISM: Artificial Sequence
<220> FEATURE:
<223> OTHER INFORMATION: Description of Artificial Sequence: synthetic
      peptide derived from thymic hormones
<223> OTHER INFORMATION: Xaa at positions 7-8, in the peptide's largest
      embodiment, may be ser-asn, ser-asp or ala-asn;
      the peptide may also encompass a smaller embodiment
      consisting of only ser.

<400> SEQUENCE: 24

Ala Lys Ser Gln Gly Gly Xaa Xaa
 1               5

<210> SEQ ID NO 25
<211> LENGTH: 9
<212> TYPE: PRT
<213> ORGANISM: Artificial Sequence
<220> FEATURE:
<223> OTHER INFORMATION: Description of Artificial Sequence: synthetic
      peptide derived from thymic hormones
<223> OTHER INFORMATION: Xaa at position 1 is pyro-glu.

<400> SEQUENCE: 25

Xaa Ala Lys Ser Gln Gly Gly Ser Asn
 1               5

<210> SEQ ID NO 26
<211> LENGTH: 8
<212> TYPE: PRT
<213> ORGANISM: Artificial Sequence
<220> FEATURE:
<223> OTHER INFORMATION: Description of Artificial Sequence: synthetic
``` peptide derived from thymic hormones

<400> SEQUENCE: 26

Ala Lys Ser Gln Gly Gly Ser Asn
 1               5

<210> SEQ ID NO 27
<211> LENGTH: 4
<212> TYPE: PRT
<213> ORGANISM: Artificial Sequence
<220> FEATURE:
<223> OTHER INFORMATION: Description of Artificial Sequence: synthetic
      peptide derived from thymic hormones
<223> OTHER INFORMATION: Xaa at position 3 is ser(But).
<223> OTHER INFORMATION: Xaa at position 4 is asn(O-But).

<400> SEQUENCE: 27

Gly Gly Xaa Xaa
 1

<210> SEQ ID NO 28
<211> LENGTH: 4
<212> TYPE: PRT
<213> ORGANISM: Artificial Sequence
<220> FEATURE:
<223> OTHER INFORMATION: Description of Artificial Sequence: synthetic
      peptide derived from thymic hormones
<223> OTHER INFORMATION: Xaa at position 2 is lys(Boc).
<223> OTHER INFORMATION: Xaa at position 3 is ser(But).
<223> OTHER INFORMATION: Xaa at position 4 is gln(Mbh).

<400> SEQUENCE: 28

Ala Xaa Xaa Xaa
 1

<210> SEQ ID NO 29
<211> LENGTH: 4
<212> TYPE: PRT
<213> ORGANISM: Artificial Sequence
<220> FEATURE:
<223> OTHER INFORMATION: Description of Artificial Sequence: synthetic
      peptide derived from thymic hormones
<223> OTHER INFORMATION: Xaa at position 4 is asn(But).

<400> SEQUENCE: 29

Gly Gly Ser Xaa
 1

<210> SEQ ID NO 30
<211> LENGTH: 8
<212> TYPE: PRT
<213> ORGANISM: Artificial Sequence
<220> FEATURE:
<223> OTHER INFORMATION: Description of Artificial Sequence: synthetic
      peptide derived from thymic hormones
<223> OTHER INFORMATION: Xaa at position 2 is lys(Boc).
<223> OTHER INFORMATION: Xaa at position 3 is ser(But).
<223> OTHER INFORMATION: Xaa at position 4 is gln(Mbh)
<223> OTHER INFORMATION: Xaa at position 7 is ser(But).
<223> OTHER INFORMATION: Xaa at position 8 is asn(But).

<400> SEQUENCE: 30

Ala Xaa Xaa Xaa Gly Gly Xaa Xaa
 1               5